(12) United States Patent
Takano et al.

(10) Patent No.: US 7,566,815 B2
(45) Date of Patent: Jul. 28, 2009

(54) CONTROL OF PLANT FLOWERING TIME BY REGULATION OF PHYTOCHROME C EXPRESSION

(75) Inventors: Makoto Takano, Tsukuba (JP); Hirohiko Hirochika, Tsukuba (JP); Akio Miyao, Toride (JP)

(73) Assignee: National Institute of Agrobiological Sciences and National Agricultural and Bio-oriented Research Organization, Ibaraki (JP)

( * ) Notice: Subject to any disclaimer, the term of this patent is extended or adjusted under 35 U.S.C. 154(b) by 362 days.

(21) Appl. No.: 10/488,672

(22) PCT Filed: Aug. 30, 2002

(86) PCT No.: PCT/JP02/08824

§ 371 (c)(1),
(2), (4) Date: Aug. 19, 2004

(87) PCT Pub. No.: WO03/020935

PCT Pub. Date: Mar. 13, 2003

(65) Prior Publication Data

US 2005/0066393 A1    Mar. 24, 2005

(30) Foreign Application Priority Data

Sep. 3, 2001    (JP)    ............................ 2001-266330

(51) Int. Cl.
*C12N 15/82*    (2006.01)
*A01H 5/00*    (2006.01)
*A01H 5/10*    (2006.01)

(52) U.S. Cl. ..................... 800/290; 800/278; 800/285; 800/286; 800/298

(58) Field of Classification Search ................ 536/23.1, 536/23.6, 24.5; 800/298, 278, 290, 286, 800/285; 435/320.1, 419
See application file for complete search history.

(56) References Cited

OTHER PUBLICATIONS

Colliver et al (1997, Plant Mol. Biol. 35:509-522).*
Montgomery et al (Trends in Genetics, Jul. 1998, 14(7):255-258).*
Emery et al (2003, Current Biology 13:1768-1774).*
Hirschfeld et al (1998, Genetics 149:523-535).*
Palecanda et al (2001, Plant Molecular Biology 46:89-97).*
Basu et al (2000, Plant Molecular Biology 44:27-42).*
Basu et al. "Rice PHYC gene: structure, expression, map position and evolution." *Plant Mol Biol.* Sep. 2000;44(1):27-42.
Izawa et al. "Phytochromes confer the photoperiodic control of flowering in rice (a short-day plant)." *Plant J.* Jun. 2000;22(5):391-9.
genBank Acc. No. AB018442 for Oryza sativa (japonica cultivar-group) mRNA for phytochrome C, complete cds, 2005.
Franklin, K.A., et al. "Mutant analyses define multiple roles for phytochrome C in Arabidopsis photomorphogenesis." *Plant Cell.* Sep. 2003; 15(9):1981-9.
Halliday, K.J., et al. "Expression of heterologous phytochromes A, B or C in transgenic tobacco plants alters vegetative development and flowering time." *Plant J.* Nov. 1997; 12(5):1079-90.
Izawa, T., et al. "Phytochrome mediates the external light signal to repress FT orthologs in photoperiodic flowering of rice." *Genes Dev.* Aug. 1, 2002; 16(15):2006-20.
Isolation and characterization of phyC mutants in Arabidopsis reveals complex crosstalk between phytochrome signaling pathways. *Plant Cell.* Sep. 2003; 15(9):1962-80.
Qin, M., et al. "Overexpressed phytochrome C has similar photosensory specificity to phytochrome B but a distinctive capacity to enhance primary leaf expansion." *Plant J.* Nov. 1997; 12(5):1163-72.
Sharrock, R.A., et al. "Novel phytochrome sequences in Arabidopsis thaliana: structure, evolution, and differential expression of a plant regulatory photoreceptor family." *Genes Dev.* Nov. 1989; 3(11):1745-57.
Childs, Kevin L. et al., "The Sorghum Photoperiod Sensitivity Gene, $Ma_3$, Encodes a Phytochrome $B^1$," *Plant Physiol.*, vol. 113:611-619 (1997).
Takano, Makoto et al., "Isolation and Characterization of Rice Phytochrome A Mutants," *The Plant Cell*, vol. 13:521-534 (2001).

* cited by examiner

*Primary Examiner*—Stuart F. Baum
(74) *Attorney, Agent, or Firm*—Lahive & Cockfield, LLP; Elizabeth A. Hanley, Esq.; Jeanne M. DiGiorgio, Esq.

(57) ABSTRACT

Rice phyC mutants were isolated using a mutant panel isolation method. When the mutants were grown under long-day photoperiodic conditions, it was found that they flowered (exposed their panicles (heads)) about one week earlier than the control rice. The results indicate that suppression of PHYC gene expression can promote plant flowering under long-day conditions. Utilization of the PHYC gene for promoting plant flowering will contribute substantially to breed improvement, for example, by facilitating the creation of useful agricultural crops and decorative plants that have a new characteristic adaptable for other cultivation areas and times. The rice phyC mutants described herein, which promote flowering under long-day conditions, will be highly prized as a new early-harvest rice cultivar.

5 Claims, 6 Drawing Sheets

```
MSSSRSNNRA TCSRSSSARS KHSARVVAQT PMDAQLHAEF EGSQRHFDYS     50
SSVGAANRSG ATTSNVSAYL QNMQRGRFVQ PFGCLLAVHP ETFALLAYSE    100
NAAEMLDLTP HAVPTIDQRE ALAVGTDVRT LFRSHSFVAL QKAATFGDVN    150
LLNPILVHAR TSGKPFYAIM HRIDVGLVID LEPVNPVDLP VTATGAIKSY    200
KLAARAIARL QSLPSGNLSL LCDVLVREVS ELTGYDRVMA YKFHEDEHGE    250
VIAECKRSDL EPYLGLHYPA TDIPQASRFL FMKNKVRMIC DCSATPVKII    300
QDDSLTQPIS ICGSTLRAPH GCHAQYMASM GSVASLVMSV TINEDEDDDG    350
DTGSDQQPKG RKLWGLMVCH HTSPRFVPFP LRYACEFLLQ VFGIQINKEV    400
ELAAQAKERH ILRTQTLLCD MLLRDAPVGI FTQSPNVMDL VKCDGAALYY    450
QNQLWVLGST PSEAEIKNIV AWLQEYHDGS TGLSTDSLVE AGYPGAAALG    500
DVVCGMAAIK ISSKDFIFWF RSHTAKEIKW GGAKHEPIDA DDNGRKMHPR    550
SSFKAFLEVV KWRSVPWEDV EMDAIHSLQL ILRGSLQDED ANKNNNAKSI    600
VTAPSDDMKK IQGLLELRTV TNEMVRLIET ATAPILAVDI TGSINGWNNK    650
AAELTGLPVM EAIGKPLVDL VIDDSVEVVK QILNSALQGI EEQNLQIKLK    700
TFNHQENNGP VILMVNACCS RDLSEKVVGV CFVAQDMTGQ NIIMDKYTRI    750
QGDYVAIVKN PSELIPPIFM INDLGSCLEW NEAMQKITGI KREDAVDKLL    800
IGEVFTHHEY GCRVKDHGTL TKLSILMNTV ISGQDPEKLL FGFFNTDGKY    850
IESLMTATKR TDAEGKITGA LCFLHVASPE LQHALQVQKM SEQAAMNSFK    900
ELTYIRQELR NPLNGMQFTR NLLEPSDLTE EQRKLLASNV LCQEQLKKIL    950
HDTDLESIEQ CYTEMSTVDF NLEEALNTVL MQAMPQSKEK QISIDRDWPA   1000
EVSCMHLCGD NLRLQQVLAD FLACMLQFTQ PAEGPIVLQV IPRMENIGSG   1050
MQIAHLEFRL VHPAPGVPEA LIQEMFRHSP GASREGLGLY ISQKLVKTMS   1100
GTVQYLRESE SSSFIVLVEF PVAQLSTKRC KASTSKF                1137
```

B

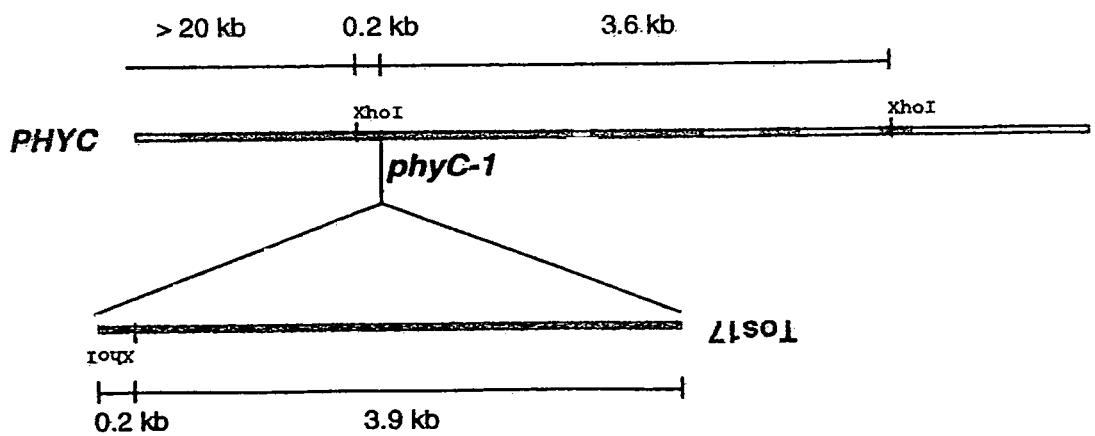

CONTROL OF PLANT FLOWERING TIME BY REGULATION OF PHYTOCHROME C EXPRESSION

RELATED APPLICATIONS

This application is a 35 U.S.C. §371 national stage filing of International Application No. PCT/JP02/08824, filed 30 Aug. 2002, which claims priority to Japanese Patent Application No. 2001-266330 filed on 03 Sep. 2001 in Japan. The contents of the aforementioned applications hereby incorporated by reference.

TECHNICAL FIELD

The present invention relates to utilization of the PHYC gene, which is involved in the regulation of plant flowering (heading) time.

BACKGROUND ART

Rice is a short-day plant, meaning it flowers (exposes its panicle (head)) when day-length becomes short. Photoreceptors that sense the day-length are called phytochrome (phy), pigment binding molecules. In rice there are three phytochrome encoding genes, PHYA, PHYB, and PHYC (Kay, S. A. et al., Nucleic Acids Res. 17: 2865-2866, 1989, Dehesh, K. et al., Mol. Gen. Genet. 225: 305-313, 1991, Tahir, M. et al., Plant Physiol. 118: 1535, 1998).

As a phytochrome mutant in monocots such as rice, a phyB mutant ($ma_3^R$) has been isolated from sorghum (Childs, K. L. et al., Plant Physiol. 113: 611-619, 1997). The $ma_3^R$ mutant shows the early-flowering phenotype as well as characteristic phenotypes such as reduced chlorophyll content, stem elongation, and acceleration of apical dominance, which are obviously different from the normal plant type. Recently, the present inventors isolated phyA mutants from rice and analyzed their detailed phenotypes. As a result, no significant difference was observed in the flowering time of the mutant rice as compared to the control rice, *Nipponbare*, under either long-day or short-day photoperiodic conditions (Takano, M. et al., Plant Cell 13: 521-534, 2001). The se5 mutant of rice, in which levels of all phytochromes are reduced to below detectable levels, showed an early-flowering phenotype regardless of day-length photoperiod conditions (Izawa, T. et al., Plant J. 22: 391-339, 2000). However, in this mutant, all phytochrome genes, PHYA, PHYB, and PHYC, were unaltered though a mutation was found in the plastid heme oxidase encoding gene (Izawa, T. et al., Plant J. 22: 391-339, 2000).

Thus far, there has been no report of the isolation of a phyC mutant, even from the well-known experimental model plant *Arabidopsis thaliana*, and no report of a functional analysis of PHYC gene in relation to plant flowering time.

DISCLOSURE OF THE INVENTION

The present invention has been developed through contemplation of the background as mentioned above. An objective of the present invention is to isolate phyC mutants and analyze their phenotypes to provide a method for PHYC gene utilization. Specifically, the present invention aims at providing phyC mutants that hasten the onset of flowering (heading) and a method to accelerate flowering by suppressing the PHYC gene expression.

The present inventors have conducted exhaustive research to achieve the above objectives. To elucidate the function of the PHYC gene, phyC mutants were obtained using a mutant isolation method with mutant panels (Hirochika, H. In: Molecular Biology of Rice, Springer-Verelag (Tokyo), pp. 43-58, 1999).

In this system, insertional mutant lines were obtained by activating retrotransposon Tos17 in tissue cultures of rice, a short-day plant. It is known that when rice seeds are tissue cultured, a retrotransposon in the rice genome called Tos17 becomes activated and disrupts genes by transposition into other chromosomal regions. By forming calluses from the seeds to regenerate mature plants, a large number of independent mutant lines can easily be generated.

The mutants of interest were isolated among such generated mutant lines. Specifically, each collection of 980 mutant lines was placed in a three dimensional matrix called a mutant panel that resembles ten microtiter plates piled to form a Z-axis of eight rows, a Y-axis of-twelve rows, and an X-axis of ten rows. DNA was extracted from a pool of mutant lines on each axis, and used in screening for mutants of interest. These pooled DNAs were used as templates for PCR that contained a set of primers specific to the PHYC gene and to the LTR regions of Tos17. An amplified band was obtained only when the Tos17 retrotransposon was present near the primer specific to the PHYC gene (i.e., Tos17 was inserted within the PHYC gene). In this way, only eight PCR amplifications were needed to determine whether a mutant of interest was contained in a panel, i.e., the 980 mutant lines. When a specific band was amplified, the same combination of primers was utilized for PCR on X and Y-axes in the same panel. A row where amplification was found was confirmed on each axis. The location of the mutant of interest was determined from the crossing point of such rows within the three dimensional matrix.

From the experiments, a phyC mutant was successfully isolated in which Tos17 was inserted in the coding region at the first exon of the PHYC gene. Furthermore, it was found that the phyC mutant initiated flowering (heading) approximately one week earlier as compared to the control rice when grown under long-day conditions. Therefore, it was elucidated for the first time that the PHYC gene product is involved in sensing long-day photoperiods to delay flowering. To date, there has been no report of involvement of the PHYC gene in the determination of plant flowering time. The results herein suggest that suppressing the PHYC gene expression will enable the promotion of plant flowering under long-day conditions. Notably, there are no significant differences in phenotype, with the exception of flowering time, in the phyC mutant as compared to the wild-type, so it has an advantage of specifically driving early flowering through the suppression of the gene expression. Utilization of the PHYC gene to promote flowering will contribute substantially to breed improvement, for example, by facilitating the creation of useful agricultural crops and decorative plants that have a new characteristic adaptable for other cultivation areas and times. In addition, the rice phyC mutant, which flowers earlier under long-day conditions, will be highly prized as a new early-harvesting rice cultivar.

Namely, the present invention relates to the utilization of the PHYC gene, which controls plant flowering (heading) time under long-day conditions, to promote flowering, specifically, (1) a nucleic acid that promotes flowering of a plant, wherein said nucleic acid is selected from any one of (a) to (c):

(a) an antisense nucleic acid complementary to a plant PHYC transcript;

(b) a nucleic acid having ribozyme activity that specifically cleaves the plant PHYC transcript; and (c) a nucleic acid that inhibits a plant phyC gene expression through co-suppression;

(2) the nucleic acid of (1), wherein the plant is a short-day plant;

(3) the nucleic acid of (2), wherein the short-day plant is rice;

(4) a vector comprising the nucleic acid of any one of (1) to (3);

(5) a transformed plant cell carrying the nucleic acid of any one of (1) to (3) or the vector of (4);

(6) a transgenic plant comprising the transformed plant cell of (5);

(7) a transgenic plant that is a progeny or a clone of the transgenic plant of (6);

(8) a reproducing material of the transgenic plant of (6) or 7;

(9) a method for producing the transgenic plant of (6) or (7) wherein the method comprises the step of introducing the nucleic acid of any one of (1) to (3) or the vector of (4) into a plant cell, and regenerating a plant from the plant cell;

(10) a method for promoting flowering-of a plant, wherein the method comprises suppressing endogenous PHYC gene expression in cells of the plant;

(11) the method of (10), wherein the method comprises introducing the nucleic acid of any one of (1) to (3) or the vector of (4) into the plant;

(12) the method of any one of (9) to (11), wherein the plant is a short-day plant;

(13) the method of (12), wherein the short-day plant is rice;

(14) a rice phyC mutant;

(15) a rice phyC mutant that is a progeny or clone of the mutant of (14); and

(16) a reproducing material of the rice phyC mutant of (14) or (15).

The present inventors have elucidated that the rice phyC mutation can promote rice flowering (heading) under long-day conditions. This indicates that it is possible to promote plant flowering under long-day conditions by suppressing plant PHYC gene expression.

The present invention provides nucleic acids that promote plant flowering. In a preferred embodiment of the present invention, plant flowering is promoted under long-day conditions by suppressing PHYC gene expression.

Generally, the term "flowering" means that flowers open; however, in the context of the present invention, as the term "flowering" applies to plants of the rice family including rice, for example, the term flowering means that panicles (heads) emerge. In the present invention the phrase "promote flowering" means to advance the onset of flowering. In the present invention, the phrase "long-day conditions" refers to photoperiodic conditions where a dark period in a day is shorter than a threshold dark period required for photoperiodic responses (critical dark period) Specifically, a 14-hour light/10-hour dark photoperiod is generally used as an example.

In the present invention, the above-mentioned PHYC gene is a gene encoding a phyC protein, which is one of plant pigment binding proteins, phytochtome. The PHYC gene is found in various plants. Therefore, in the present invention, it is possible to promote flowering in a desired plant by suppressing PHYC gene expression of the plant. In the present invention, the plant chosen to have flowering promoted under long-day conditions by regulating PHYC gene expression is preferably a short-day plant and more preferably a plant belonging to the rice family. A specifically preferred example is rice. A short-day plant is a plant that forms flower buds or whose flower bud formation is promoted under photoperiodic conditions where an uninterrupted dark period is longer than the critical dark period. Preferably, plants whose flowering may be promoted by this invention are, for example, useful agricultural crops and decorative plants. In concrete terms, useful agricultural crops may be monocot plants, such as rice, or dicot plants, such as soybean. Decorative plants may be flowering plants, such as chrysanthemum, morning glory, poinsettia, and cosmos.

The PHYC genes in the present invention include rice PHYC gene (Genbank accession number: AB018442) and *Arabidopsis thaliana* PHYC gene (Genbank accession number: Z32538) as working examples.

Furthermore, using methods known to one skilled in the art, such as hybridization technique (Southern, E. M. et al., Journal of Molecular Biology 98: 503, 1975) or polymerase chain reaction (PCR) techniques (Saiki, R. K. et al., Science 230: 1350-1354, 1985, Saiki, R. K. et al., Science 239: 487-491, 1988), homologues of the above-mentioned PHYC gene can be isolated, and the nucleotide sequence information of such genes can be obtained. For example, hybridization technique using the rice PHYC gene nucleotide sequence (Genbank accession number: AB018442) or its partial sequence as a probe, or PCR technique using specific oligonucleotide as a primer to hybridize to the PHYC gene enables one to isolate DNA highly homologous to the PHYC gene from a desired plant.

To isolate such DNA, the hybridization reaction is generally carried out under stringent conditions. Hybridization conditions of 6 M urea, 0.4% SDS, and 0.5×SSC, or equivalent conditions can be used as stringent conditions. Employing even higher stringency conditions, such as 6 M urea, 0.4% SDS, and 0.1×SSC, may enable one to obtain highly homologous DNA. The sequence of the isolated DNA can be determined by a known method.

Generally, the determination of whether an isolated DNA encodes a phyC protein is made based on-sequence homology. Sequence homology can be searched using programs called BLASTN (nucleic acid level) or BLASTX (amino acid level) (Altschul, S. F. et al., J. Mol. Biol. 215: 403-410, 1990). These programs are based on Karlin and Altschul's BLAST algorithm (Proc. Natl. Acad. Sci. USA 87: 2264-2268, 1990, Proc. Natl. Acad. Sci. USA 90: 5873-5877, 1993). If a nucleotide sequence is analyzed by BLASTN, parameters may be set, for example, to score=100 and wordlength=12. If an amino acid sequence is analyzed by BLASTX, parameters may be set, for example, to score=50 and wordlength=3. Amino acid sequences may be analyzed using Gapped BLAST program as described in Altschul et al. (Nucleic Acids Res. 25: 3389-3402, 1997). When BLAST and Gapped BLAST programs are used for sequence analysis, the default parameters of the respective programs are used. These specific analytical methods are widely known.

In a method of the present invention, to generate a plant with promoted flowering, DNA that suppresses PHYC gene expression is inserted into an appropriate vector and introduced into plant cells from which whole plants are regenerated. The phrase "suppression of PHYC gene expression" encompasses both transcriptional and translational suppression, and includes not only complete cessation of the DNA expression but also a reduction in the expression level.

In the present invention, to suppress expression of an endogenous plant gene, one skilled in art may utilize, for example, an antisense technique. The efficacy of the antisense technique in plant cells was proven by Ecker et al. for the first time when antisense RNA was introduced by electroporation using transient gene expression (Ecker, J. R. and Davis, R. W. Proc. Natl. Acad. Sci USA 83: 5372, 1986). Later, the antisense effect was also observed in tobacco and petunia for reduction of expression of a target gene (Krol, A. R. et al., Nature 333: 866, 1988). Today, it is an established technique for suppressing plant gene expression. There are multiple mechanisms for suppressing target gene expression by antisense nucleic acids, namely: inhibition of transcription initiation by triple strand formation; transcription suppression caused by hybrid formation at a site where an RNA polymerase has formed a local open loop structure; transcription inhibition caused by hybridization to RNA being synthesized; splicing suppression caused by hybrid formation at a junction between an intron and exon; splicing suppression caused by hybrid formation at a spliceosome site; suppression of mRNA translocation from the nucleus to cytoplasm by hybrid formation with mRNA; splicing suppression by hybridization at a capping site or poly A addition site; suppression of translation initiation by hybrid formation at a translation initiation factor binding site; translation suppression caused by hybridization to a ribosome binding site near an initiation codon; peptide extension inhibition by hybridizing within a translated region or polysome binding site of mRNA; suppression of gene expression by hybrid formation at a site where nucleic acid and protein interact; etc. These various mechanisms inhibit the processes of transcription, splicing, and translation of the target gene to suppress gene expression (Hirashima and Inoue, New Biochemistry Experiment Vol. 2 Nucleic acid IV, Replication and Expression of Gene, Japanese Biochemical Society ed., Tokyo Kagaku Dojin, pp. 319-347, 1993). Therefore, the present invention provides antisense nucleic acids that are complementary to plant PHYC gene transcription products. The above-mentioned antisense nucleic acids include antisense DNA, antisense RNA, and DNA encoding the antisense RNA.

In the present invention, antisense nucleic acids can be used for any of the above-mentioned mechanisms to suppress target gene expression. In one embodiment, an antisense nucleic acid designed to be complementary to the 5' untranslated region of mRNA allows for effective for translation inhibition. However, nucleic acids complementary to the coding region or 3' untranslated region may be also utilized. Antisense DNA designed from not only translated regions but also untranslated regions may be included in the present invention. Employed antisense DNA is ligated downstream of an appropriate promoter and, preferably, a sequence comprising transcription termination signal is conjugated at its 3' end.

Antisense nucleic acids of the present invention may be prepared, for example, by the phosphorothioate method using sequence information from the DNA of SEQ ID NO: 3 (Stein, C. A. et al., Nucleic Acids Res. 16: 3209-3221, 1988). Prepared nucleic acids may be used for transfecting a desired plant by any known method. Preferably, the antisense nucleic acid sequence is complementary to the endogenous gene or a part of the gene of the transfected plant. However, so long as the gene expression can effectively be inhibited, it does not have to be completely complementary. Antisense nucleic acids of the present invention are preferably 90% or more, and most preferably 95% or more, complementary to the target gene transcript. To inhibit the target gene expression effectively using an antisense nucleic acid, the antisense nucleic acid should be at least 15 or more nucleotides in length, preferably 100 or more nucleotides, and most preferably 500 or more nucleotides in length. Antisense nucleic acids to be used are usually shorter than 5 kb and preferably shorter than 2.5 kb.

Another method for suppressing endogenous gene expression is the ribozyme technique. A ribozyme is an RNA molecule with catalytic activity. Ribozymes with various kinds of activities are known in the art. Research on ribozymes as RNA-cleaving enzymes has enabled the design of a ribozyme that cleaves RNA at a specific site. Therefore, the present invention provides nucleic acids with ribozyme activity that specifically cleave plant PHYC gene transcripts. The above-mentioned nucleic acids of the present invention include RNA with ribozyme activity and DNA that encodes such RNA.

While ribozymes, such as those of the group I intron type and m1RNA contained in RnaseP, can be large, with 400 nucleotides or more, there are smaller ones as well, including the hammerhead type and hairpin type having an activity domain of approximately 40 nucleotides (Koizumi, M. and Otsuka, E., Tanpakushitsu Kakusan Koso 35: 2191, 1990). For example, it is known that the self cleavage domain of a hammerhead type ribozyme cleaves at the 3' side of C15 of sequence G13U14C15. It is considered important for cleaving activity that A at $9^{th}$ position forms a base pair with U14. Furthermore, it has been shown that the cleavage also occurs when the $15^{th}$ base is A or U instead of C (Koizumi, M. et al., FEBS Lett. 228: 225, 1988). Therefore, if one designs a ribozyme to have a substrate binding site complementary to an RNA sequence close to the target site, the ribozyme can be utilized as a restriction enzyme-like RNA cleaving ribozyme to recognize the sequence UC, UU, or UA in the target RNA (Koizumi, M. et al., FEBS Lett. 239: 285, 1988, Koizumi, M. and Otsuka, E., Tanpakushitu Kakusan Koso 35: 2191, 1990, Koizumi, M. et al., Nucleic Acids Res. 17: 7059, 1989).

In addition, hairpin type ribozymes are useful in the context of the present invention. A hairpin type ribozyme can be found, for example, in the minus strand of satellite RNA in tobacco ringspot virus (Buzayan, J. M. Nature 323: 349, 1986). This ribozyme can also be designed to target-specifically cleave RNA (Kikuchi, Y and Sasaki, N. Nucleic Acids Res. 19: 6751, 1992, Kikuchi, H. Chemistry and Biology, 30: 112, 1992).

A ribozyme designed to cleave a target may be, for example, ligated to a promoter, such as cauliflower mosaic virus 35S promoter, and a transcription terminator sequence to be transcribed in plant cells. However, if unnecessary sequences are added to the 5' or 3' end of the transcribed RNA, ribozyme activity may be lost. In such a case, to accurately cut out only the ribozyme portion from a transcribed RNA comprising the ribozyme sequence, one can place another cis-acting trimming ribozyme at the 5' or 3' side of the ribozyme (Taira, K. et al., Protein Eng. 3: 733, 1990, Dzianott, A. M. and Bujarski, J. J. Proc. Natl. Acad. Sci. USA 86: 4823, 1989, Grosshans, C. A. and Cech, R. T. Nucleic Acids Res. 19: 3875, 1991, Taira, K. et al., Nucleic Acids Res. 19: 5125, 1991). In addition, multiple sites within a target gene can be cleaved by arranging such structural units in tandem to achieve greater effects (Yuyama, N. et al., Biochem. Biophys. Res. Commun. 186: 1271, 1992). Thus, one can use such ribozymes to specifically cleave a target transcript of the present invention to thereby suppress the gene expression.

Endogenous gene expression may also be suppressed by co-suppression, through transformation with a nucleic acid comprising a sequence identical or similar to the target gene sequence. "Co-suppression" refers to a phenomenon in which, when a gene having a sequence identical or similar to the target endogenous gene is introduced into plants by transformation, expression of both the target endogenous gene and introduced exogenous gene becomes suppressed. The mechanism of co-suppression is not well understood, but it is often seen in plants (Curr. Biol. 7: R793, 1997, Curr. Biol. 6: 810, 1996). Therefore, the present invention provides nucleic acids that have an inhibitory effect on plant PHYC gene expression through co-suppression. The nucleic acids of the present invention include DNA and RNA that have inhibitory effect by co-suppression.

To obtain a plant whose PHYC gene is co-suppressed using the above-mentioned nucleic acids of the present invention, for example, a vector DNA that expresses DNA comprising the PHYC gene sequence or a sequence similar to the gene is introduced into target plants followed by selection of a plant having the phyC mutant phenotype, that is, the ability to promote flowering under long-day conditions. Genes used for co-suppression do not have to be completely identical but should be at least 70% or more, preferably 80% or more, and most preferably 90% or more (for example 95% or more) identical to the target gene sequence.

Moreover, the endogenous gene suppression in the present invention may be achieved by introducing into a plant a gene that causes a dominant negative phenotype to a target gene. The "gene causing a dominant negative phenotype" refers to a gene whose expression can eliminate or reduce an activity of an endogenous wild-type gene originally present in a plant.

In addition, the present invention provides the above mentioned nucleic acids, vectors comprising the nucleic acids, transformed plant cells having the nucleic acids or vectors comprising the nucleic acids, transgenic plants containing the transformed plant cells, transgenic plants that are progeny or clones of the above transgenic plants, and breeding materials from the transgenic plants.

Moreover, the present invention provides a method for producing the above-mentioned transgenic plants that includes the process of introducing a nucleic acid of the present invention into plant cells, and regenerating plant bodies from the plant cells.

A nucleic acid of the present invention can be introduced into plant cells by one skilled in the art using known methods, for example, the agrobacterium method, electroporation method, and particle gun method.

The method of Nagel et al., for example, is used for the agrobacterium method (Microbiol. Lett. 67: 325, 1990). According to this method, agrobacterium is transformed by a recombinant vector and introduced to plant cells by a known method such as the leaf disc method. When a nucleic acid of the present invention is a DNA, the above vector comprises, for example, a promoter to express the DNA in a plant subsequent to introduction into the plant. Generally, a DNA of the present invention is placed downstream of such a promoter and, moreover, a terminator sequence is placed downstream of the DNA. A recombinant vector used for this purpose is suitably determined by one skilled in the art depending on the transfection method or the type of a plant. The above-mentioned promoter may be, for example, a cauliflower mosaic virus derived CaMV35S promoter or the ubiquitin promoter from maize (Unexamined Published Japanese Patent Application No. (JP-A) Hei 2-79983).

The above-mentioned terminator may be, for example, a cauliflower mosaic virus derived terminator or nopalin synthase terminator. However, so long as they function as a promoter or terminator in a plant, there is no limitation on them.

Plants transfected by nucleic acids of the present invention may be explants. Alternatively, cultured cells may be prepared from these plants, and such nucleic acids may be introduced into the cultured cells. "Plant cells" in the present invention may be, for example, cells from leaves, roots, stems, flowers, seed scutella, calluses, and cultured cell suspensions.

In addition, to efficiently select transformed plant cells into which a nucleic acid of the present invention has been introduced, the above recombinant vector preferably harbors an appropriate selective marker gene or is introduced into plant cells together with a plasmid vector harboring a selective marker gene. Selective marker genes used for this purpose include, for example, the hygromycin phosphotransferase gene, which confers resistance to the antibiotic hygromycin; the neomycin phosphotransferase gene, which confers resistance to kanamycin or gentamycin; and the acetyltransferase gene, which confers resistance to an herbicide, phosphinothricin.

Plant cells transfected with a recombinant vector are plated and cultured on a known selective medium containing an appropriate selective drug, depending on the type of the introduced selective marker gene. In this way, one can obtain transformed plant cultured cells.

Next, a plant body is regenerated from the transformed plant cells into which a nucleic acid of the present invention has been introduced. Regeneration of a plant can be carried out by methods known to one skilled in the art depending on the plant cell type (Toki et al., Plant Physiol. 100: 1503-1507, 1995). Several techniques have already been established to generate transformed rice plants, and those techniques are widely used in the field of the present invention. For example, rice plants can be regenerated after (1) genes are introduced into protoplasts using polyethylene glycol (suitable for Indica rice varieties) (Datta, S. K. et al., In Gene Transfer To Plants (Potrykus I and Spangenberg Eds.) pp 66-74, 1995); (2) genes are introduced into protoplasts using electric pulse (suitable for Japonica rice varieties) (Toki et al., Plant Physiol. 100: 1503-1507, 1992); (3) genes are introduced directly into cells using the particle gun method (Christou et al., Bio/technology, 9: 957-962, 1991); or (4) genes are introduced using agrobacteria (Hiei et al., Plant J. 6: 271-282, 1994). In the present invention, these methods can preferably be used.

The plants regenerated from transformed plant cells are subsequently cultured in acclimatization medium. Then, after the acclimatized regenerated plants are grown under the normal cultivation conditions, flowering-promoted plants can be obtained. Seeds can also be obtained when these plants mature and fruit.

The exogenously introduced nucleic acid in a thus regenerated and grown transgenic plant can be confirmed by known methods, such as PCR or Southern hybridization, or by analyzing the nucleotide sequence of the nucleic acid from the plant. To extract nucleic acid from a transgenic plant, the known method of J. Sambrook et al. may be used (Molecular Cloning, $2^{nd}$ edition, Cold Spring Harbor laboratory Press, 1989).

To conduct PCR analysis of the exogenous gene comprising a nucleic acid of the present invention, which exists in the regenerated plant body, an amplification reaction is carried out using the template nucleic acid that was extracted from the regenerated plant by the above-mentioned method. When the nucleic acid of the present invention is DNA, the amplification reaction may be carried out in a reaction mixture containing as primers synthesized oligonucleotides having nucleotide sequences that are appropriately selected according to a nucleotide sequence of the DNA. An amplified DNA fragment comprising a DNA sequence of the present invention may be obtained by repeating the denaturation, annealing, and extension steps for DNA several ten cycles in the amplification reaction. The respective amplified DNA fragments can be separated by, for example, electrophoresing the reaction solution containing amplified products on agarose gel. It is then possible to confirm the DNA fragment corresponding to DNA of the present invention.

Once a transgenic plant in which a nucleic acid of the present invention has been inserted into the chromosomes is obtained, one can obtain the plant progeny by sexual or non-sexual reproduction. Also, it is possible to mass-produce such plants by obtaining reproductive materials (such as seeds, fruits, cuttings, stem tubers, root tubers, shoots, calluses, and protoplasts) from the above plant, or its progeny or clone.

In the present invention, as mentioned above, by suppressing PHYC gene expression, plant flowering can be promoted.

Moreover, the present invention provides rice phyC mutants, their progeny or clones, and reproductive materials of the phyC mutants.

The rice phyC mutants in the present invention include not only the rice phyC mutants that can promote flowering under long-day conditions (homozygous mutants), but also heterozygous mutants. The heterozygous mutants are useful for generating homozygous mutants. In addition, the rice phyC mutants in the present invention include, besides the phyC mutants (homozygous and heterozygous mutants) isolated in the present invention, phyC mutants (homozygous and heterozygous mutants) that will newly be isolated by using the mutant panel method described in the Examples.

BRIEF DESCRIPTION OF THE DRAWINGS

FIG. 1 shows the insertion site of the Tos17 retrotransposon in the phyC mutant. The black frame in panel A indicates the border where the Tos17 is inserted; Tos17 is inserted between histidine (H) residue 224 and glutamic acid (E) residue 245. Panel B illustrates the insertion site of Tos17 in the chromosome.

BEST MODE FOR CARRYING OUT THE INVENTION

Figure 2:
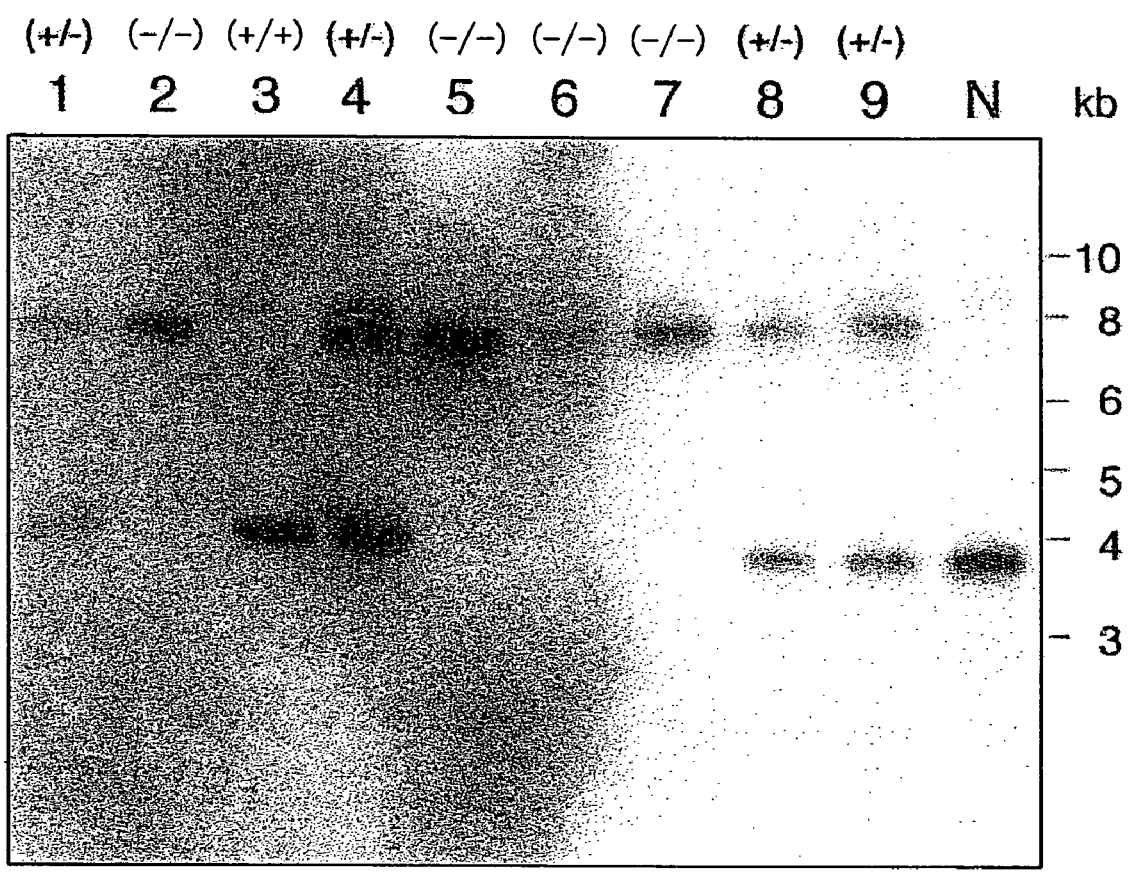
FIG. 2 shows a photograph demonstrating the isolation of phyC mutants. A heterozygous mutant of the phyC mutation was self fertilized, and resulting offspring (#1-9) were analyzed by Southern hybridization using a probe detecting a 3.8 kb fragment containing PHYC gene, which would be yielded by XhoI-treatment. (+/+): wild-type, (+/−): heterozygous phyC mutant, and (−/−): homozygous phyC mutant.

The present invention will be explained in detail below with reference to the examples below but is not intended to be limited to these examples.

EXAMPLE 1

Isolation of phyC Mutant

The present inventors isolated phyC mutants using the mutant panel method. PHYC gene primers were designed based on the rice PHYC cDNA sequence (Genbank Accession number: AB018442). Six primers were designed to cover the whole sequence of the phyC gene since it is a large sized gene (BR, DR, EF, FR, GF, and HR) (Table 1). Also, two primers (LTR1 and LTR4) were designed to face outward within LTR sequences at both ends of Tos17 (Table 2).

TABLE 1

| phyC-specific primer* | phy-C specific primer sequence | Primer site** |
|---|---|---|
| BR (SEQ ID NO: 1) | GTGATGGCAGACCATCAACC | 1412-1393 |
| BR1 (SEQ ID NO: 2) | CCAGTGTCTCCATCATCATCC | 1367-1347 |
| DR (SEQ ID NO: 3) | CATACCTAAGCGGGAAAGGGAC | 1449-1428 |

TABLE 1-continued

| phyC-specific primer* | phy-C specific primer sequence | Primer site** |
|---|---|---|
| DR1 (SEQ ID NO: 4) | AAAGGGACAAACCTCGGGCTTG | 1435-1414 |
| EF (SEQ ID NO: 5) | CGTACAAGTTCCATGAGGATGAGC | 1018-1041 |
| EF1 (SEQ ID NO: 6) | GAGGTGATTGCTGAGTGCAAGAG | 1047-1069 |
| FR (SEQ ID NO: 7) | ATCGACCAGAGGCTTCCCTATG | 2306-2285 |
| FR1 (SEQ ID NO: 8) | TGGCTTCCATGACAGGTAATCC | 2286-2265 |
| GF (SEQ ID NO: 9) | GCCTAATTGAGACAGCAACTGCG | 2176-2198 |
| GF1 (SEQ ID NO: 10) | TTGGCTGTTGACATCACTGG | 2205-2224 |
| HR (SEQ ID NO: 11) | ACGAGCTTCTGGCTTATGTAAAGG | 3586-3563 |
| HR1 (SEQ ID NO: 12) | TGGCGGAACATCTCTTGTATCAG | 3532-3510 |

*BR1, DR1, EF1, FR1, GF1, and HR1 indicate nested PCR primers for BR, DR, EF, FR, GF, and HR, respectively.
**Primer site in the rice PHYC gene cDNA sequence (Genbank Accession number: AB018442)

TABLE 2

| Tos17 specific primer* | Tos17 specific primer sequence |
|---|---|
| LTR1 (SEQ ID NO: 13) | TTGGATCTTGTATCTTGTATATAC |
| LTR2 (SEQ ID NO: 14) | GCTAATACTATTGTTAGGTTGCAA |
| LTR4 (SEQ ID NO: 15) | CTGGACATGGGCCAACTATACAGT |
| LTR5 (SEQ ID NO: 16) | ATTAGCTTGTATATATATTTAACA |

*LTR2 and LTR5 indicate nested PCR primers for LTR1 and LTR4, respectively.

9600 individuals on mutant panels were PCR screened by using 12 primer sets ((6 PHYC specific primers)×(2 Tos17 specific primers)). A specific amplification was observed when the BR and LTR4 primers were used. In a DNA pool for the mutant panel, DNAs derived from 80 (X-axis) to 120 (Z-axis) individuals are included, which means that the concentration of each template is very low since DNA of each individual is diluted 1/120 to 1/80. In addition, it is difficult to detect a specific amplification by one time PCR because the LTR sequence of Tos17 has a high AT content and Tm of the designed primers is low. Therefore, to increase sensitivity and specificity, additional primers (BR1, DR1, EF1, FR1, GF1, HR1, LTR2, and LTR5) were designed to correspond downstream of the above respective primers, and PCR was done twice (nested PCR) to detect amplification. As a result, a number of non-specific bands were seen, and therefore, Southern hybridization was carried out to identify the specific band. The identified band was excised and the DNA fragment was extracted. The DNA fragment was sequenced to determine the Tos17 insertion site. The Tos17 was inserted upstream of the chromophore (opened tetrapyrrole) binding site ($244^{th}$ amino acid) (FIG. 1), suggesting that it is a null mutant.

Also, Tos17 insertion was confirmed by Southern hybridization. When rice genomic DNA is digested with XhoI, it is expected to yield a 3.8 kb band from the wild-type rice genome based on the reported rice PHYC genomic DNA sequence (D. Basu et al. Plant Mol. Biol. 44: 27-42, 2000). In contrast, Tos17 insertional mutants are expected to yield two bands at 7.5 kb and 0.4 kb, respectively. DNA was extracted from progeny (#1-9) of self fertilized phyC heterozygous mutants and subjected to Southern hybridization using a probe that recognizes the 3.8 kb fragment containing the PHYC gene, which would be yielded by XhoI treatment (for mutants, using a probe comprising the full-length phyC cDNA, which recognizes the 7.5 kb fragment). The expected results were obtained. In addition, it was found that the Tos17 insertional mutation was segregated into homozygous mutants (#2, 5, 6, and 7) and heterozygous mutants (#1, 4, 8, and 9), and that the Tos17 was missing in #3 (FIG. 2). As known from these results, one phyC mutant line (osphyC-1) was obtained.

EXAMPLE 2

Confirmation of PHYC Gene Transcript by RT-PCR

Figure 3:
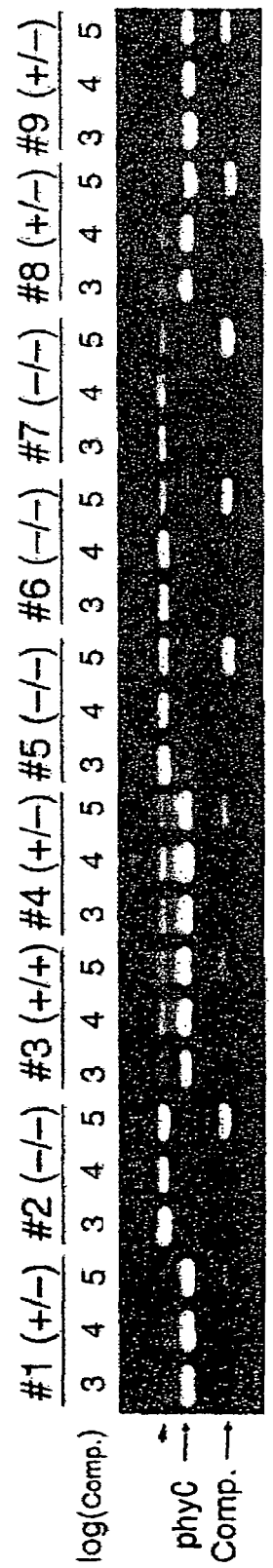
FIG. 3 shows the expression level of the PHYC gene transcript using the competitive RT-PCR method. log(Comp) indicates logarithms of competitor concentrations. PhyC indicates PHYC transcripts, and Comp indicates amplified products derived from competitor sequence. (+/+) wild-type, (+/−): heterozygous phyC mutant, and (−/−): homozygous phyC mutant.

To confirm a lack of PHYC gene expression in the isolated phyC mutants, a heterozygous phyC mutant was self-pollinated, and DNAs were extracted from its progeny (#1-9) to determine their genotypes. In addition, RNAs were extracted to conduct competitive RT-PCR using BR and EF primers described in Table 1 (FIG. 3). As a competitor DNA, a DNA fragment which harbors BR and EF sequences at both ends and, between them, a 340 bp sequence unrelated to phyC cDNA, was used. As a result, the PHYC gene was amplified from wild-type (#3) or heterozygous phyC mutants (#1, 4, 8, and 9) but homozygous phyC mutants (#2, 5, 6, and 7) did not show a band at the expected size, indicating no PHYC gene expression.

EXAMPLE 3

Effect of phyC Mutation on Flowering (Heading) Time

Figure 4:
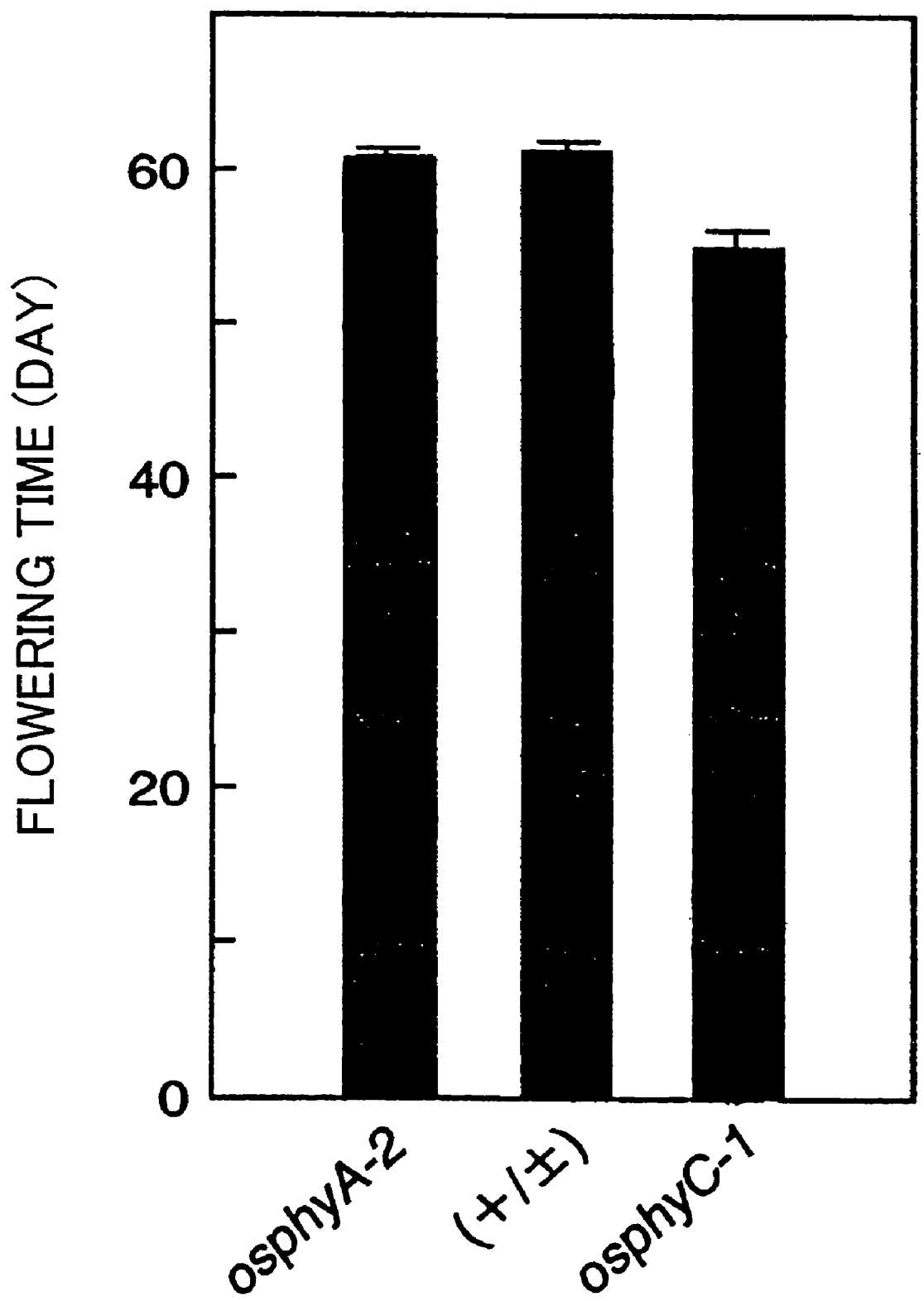
FIG. 4 shows the flowering (heading) time of the phyC mutants grown in a field. osphyA-2: phyA mutant, (+/±): wild-type or heterozygous mutant segregated after self fertilization, osphyC-1: phyC mutant.

To investigate flowering time, *Nipponbare* and phyC mutant seeds were sowed on Jun. 28, 2000 and transplanted into a field on Jul. 14, 2000. These rice plants were grown under natural day lengths and the time of flowering was observed. As shown in FIG. 4, a phyA mutant (osphyA-2) control, and wild-type or heterozygous mutant segregants from the self fertilized phyC mutant flowered on the $60^{th}$ to $61^{st}$ day after sowing, while, the phyC mutants flowered on the $54^{th}$ day, about a week earlier.

Figure 5:
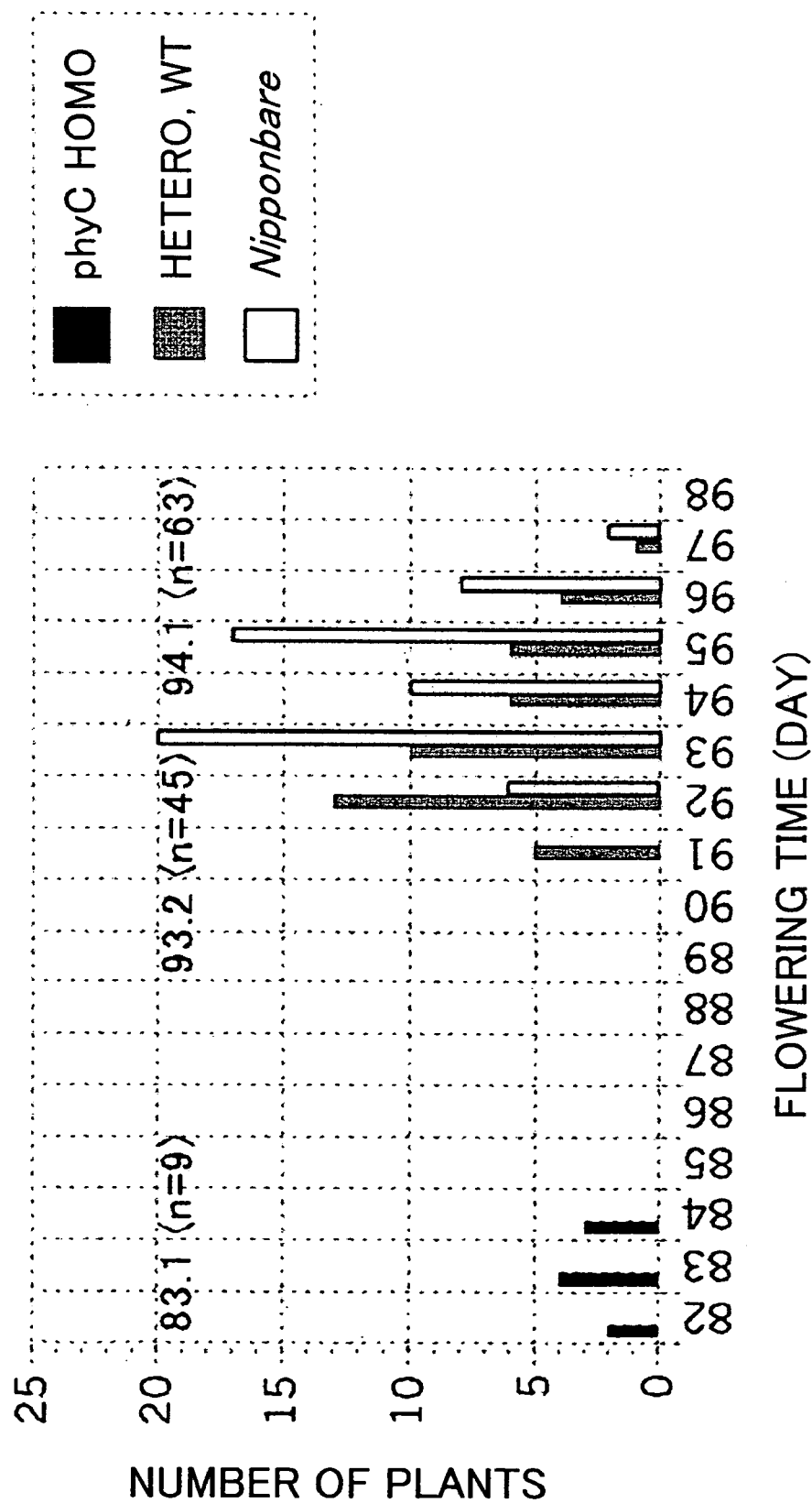
FIG. 5 shows the relationship between flowering time and genotypes of the F2 group segregants of phyC mutant backcrossed with *Nipponbare*.

In addition, to confirm the linkage between the phyC mutation and earlier flowering time, the phyC mutant was back-crossed with *Nipponbare*, and the genotype and flowering time of its F2 group segregants were investigated. The F2 group (n=54) and control *Nipponbare* group (n=63) were sown on May 15, 2002 and transplanted into a field on Jun. 5, 2002. As shown in FIG. 5, the segregated heterozygous and wild-type individuals (n=45) flowered after an average of 93.2 days and no earlier than the $91^{st}$ day after sowing. On the other hand, the phyC mutants (n=9) flowered after an average of 83.1 days and no later than the $84^{th}$ day. The genotype completely correlated with the flowering time in this group. The control *Nipponbare* flowered after 94.1 days on average, which was almost identical to the flowering time of heterozygous and wild-type individuals.

Figure 6:
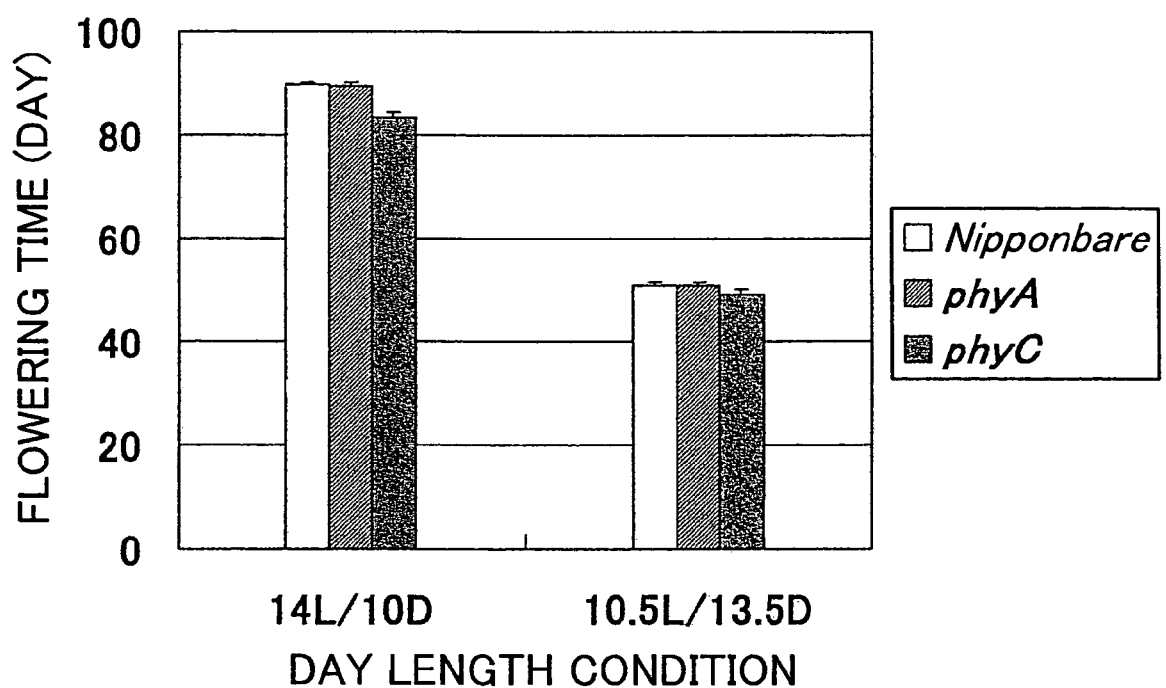
FIG. 6 shows the flowering (heading) time of phyC mutant under long-day and short-day photoperiodic conditions. 14L/10D and 10.5L/13.5D in the horizontal axis indicate long-day and short-day conditions, respectively.

Furthermore, to test flowering time under short-day and long-day conditions, the plants were grown in a climate-control incubator (short-day: 10.5-hour light/13.5-hour dark, long-day: 14-hour light/10-hour dark) (FIG. 6). Under short-day conditions, there was no difference among *Nipponbare*, phyA mutants, and phyC mutants. All of them flowered after approximately 50 days. Under long-day conditions, *Nipponbare* and the phyA mutants took about 90 days to flower, while, the phyC mutants flowered after about 83 days, about a week earlier. Therefore, the PHYC gene is considered to sense a long-day photoperiod and function to slow flowering.

In addition, the phyC mutants were investigated for phenotypic differences, apart from flowering time, such as plant height, plant feature, chlorophyll content, and chlorophyll a/b ratio; however, no significant difference was observed.

INDUSTRIAL APPLICABILITY

The present invention provides a method for promoting flowering (heading) using a plant PHYC gene. A phyC mutant that does not show phenotypic changes (for example changes of plant height, plant feature, chlorophyll content, and chlorophyll a/b ratio) other than flowering time is described herein. As such, it appears that suppression of PHYC expression can specifically promote flowering. Utilization of the PHYC gene to promote flowering will contribute substantially to breed improvement, for example, by facilitating the creation of useful agricultural crops and decorative plants that have a new characteristic adaptable for other cultivation areas and times. The present invention also provides a plant phyC mutant whose flowering is promoted under long-day photoperiodic conditions. The rice phyC mutant will be highly prized as a new early-harvest rice cultivar.

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 1
gtgatggcag accatcaacc                                              20

```
<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 2
ccagtgtctc catcatcatc c                                              21

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 3
catacctaag cgggaaaggg ac                                             22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 4
aaagggacaa acctcgggct tg                                             22

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 5
cgtacaagtt ccatgaggat gagc                                           24

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 6
gaggtgattg ctgagtgcaa gag                                            23

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 7
atcgaccaga ggcttcccta tg                                             22

<210> SEQ ID NO 8
```

```
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 8
tggcttccat gacaggtaat cc                                              22

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 9
gcctaattga gacagcaact gcg                                             23

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 10
ttggctgttg acatcactgg                                                 20

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 11
acgagcttct ggcttatgta aagg                                            24

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 12
tggcggaaca tctcttgtat cag                                             23

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 13
ttggatcttg tatcttgtat atac                                            24

<210> SEQ ID NO 14
<211> LENGTH: 24
```

```
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 14
gctaatacta ttgttaggtt gcaa                                              24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 15
ctggacatgg gccaactata cagt                                              24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 16
attagcttgt atatatattt aaca                                              24
```

The invention claimed is:

1. A method for promoting flowering of a rice plant, wherein the method comprises introducing an isolated nucleic acid into the plant, wherein the nucleic acid inhibits the expression of the rice PHYC gene of SEQ ID NO:17, thereby promoting flowering of the plant, and is:
   (a) an antisense nucleic acid selected from the group consisting of:
       (i) the antisense nucleic acid that is complementary to the rice PHYC gene of SEQ ID NO:17 transcript; and
       (ii) an antisense nucleic acid that is the complement of a nucleic acid that is 95% identical to the rice PHYC gene of SEQ ID NO:17 transcript; or
   (b) a nucleic acid that inhibits a rice plant phyC gene expression through co-suppression selected from the group consisting of:
       (i) an isolated rice PHYC gene of SEQ ID NO:17; and
       (ii) a nucleic acid that is at least 95% identical to the rice PHYC gene of SEQ ID NO:17.

2. The method of claim 1, wherein the plant is a short-day plant.

3. A transgenic plant produced by the method of claim 1.

4. A transgenic plant that is a progeny or a clone of the parent transgenic plant of claim 3, wherein the progeny or clone comprises the nucleic acid that was introduced into the parent plant.

5. A reproducing material of the transgenic plant of claim 3 or 4, wherein the reproducing material comprises the nucleic acid that was introduced into the transgenic plant.

* * * * *

UNITED STATES PATENT AND TRADEMARK OFFICE
CERTIFICATE OF CORRECTION

PATENT NO. : 7,566,815 B2
APPLICATION NO. : 10/488672
DATED : July 28, 2009
INVENTOR(S) : Makoto Takano et al.

It is certified that error appears in the above-identified patent and that said Letters Patent is hereby corrected as shown below:

Title page, item [73] Assignee, please replace
"National Institute of Agrobiological Sciences and National
Agricultural and Bio-oriented Research Organization" with
--National Institute of Agrobiological Sciences, Ibaraki (JP) and National
Agriculture and Bio-oriented Research Organization, Ibaraki (JP)--.

In column 1, line number 11, please replace "applications hereby" with
--applications are hereby--.

In column 17, line number 47, please replace "phyC" with --PHYC--.

Please replace the incorrect Sequence Listing contained in the above-identified patent with the Sequence Listing set forth below.

--

```
                      SEQUENCE LISTING
<110> TAKANO, MAKOTO
      HIROCHIKA, HIROHIKO
      MIYAO, AKIO

<120> CONTROL OF PLANT FLOWERING TIME BY REGULATION OF
      PHYTOCHROME C EXPRESSION

<130> SHZ-020US

<140> 10/488,672
<141> 2004-08-19

<150> PCT/JP02/08824
<151> 2002-08-30
```

UNITED STATES PATENT AND TRADEMARK OFFICE
CERTIFICATE OF CORRECTION

PATENT NO.       : 7,566,815 B2
APPLICATION NO.  : 10/488672
DATED            : July 28, 2009
INVENTOR(S)      : Makoto Takano et al.

It is certified that error appears in the above-identified patent and that said Letters Patent is hereby corrected as shown below:

```
<150> JP 2001-266330
<151> 2001-09-03

<160> 18

<170> PatentIn Ver. 3.3

<210> 1
<211> 20
<212> DNA
<213> Artificial Sequence

<220>
<223> Description of Artificial Sequence: Synthetic
      primer

<400> 1
gtgatggcag accatcaacc                                           20

<210> 2
<211> 21
<212> DNA
<213> Artificial Sequence

<220>
<223> Description of Artificial Sequence: Synthetic
      primer

<400> 2
ccagtgtctc catcatcatc c                                         21

<210> 3
<211> 22
<212> DNA
<213> Artificial Sequence

<220>
<223> Description of Artificial Sequence: Synthetic
      primer

<400> 3
catacctaag cgggaaaggg ac                                        22

<210> 4
<211> 22
<212> DNA
<213> Artificial Sequence

<220>
<223> Description of Artificial Sequence: Synthetic
      primer
```

UNITED STATES PATENT AND TRADEMARK OFFICE
CERTIFICATE OF CORRECTION

PATENT NO. : 7,566,815 B2
APPLICATION NO. : 10/488672
DATED : July 28, 2009
INVENTOR(S) : Makoto Takano et al.

It is certified that error appears in the above-identified patent and that said Letters Patent is hereby corrected as shown below:

```
<400> 4
aaagggacaa acctcgggct tg                                             22

<210> 5
<211> 24
<212> DNA
<213> Artificial Sequence

<220>
<223> Description of Artificial Sequence: Synthetic
      primer

<400> 5
cgtacaagtt ccatgaggat gagc                                           24

<210> 6
<211> 23
<212> DNA
<213> Artificial Sequence

<220>
<223> Description of Artificial Sequence: Synthetic
      primer

<400> 6
gaggtgattg ctgagtgcaa gag                                            23

<210> 7
<211> 22
<212> DNA
<213> Artificial Sequence

<220>
<223> Description of Artificial Sequence: Synthetic
      primer

<400> 7
atcgaccaga ggcttcccta tg                                             22

<210> 8
<211> 22
<212> DNA
<213> Artificial Sequence

<220>
<223> Description of Artificial Sequence: Synthetic
      primer

<400> 8
tggcttccat gacaggtaat cc                                             22
```

UNITED STATES PATENT AND TRADEMARK OFFICE
CERTIFICATE OF CORRECTION

PATENT NO. : 7,566,815 B2
APPLICATION NO. : 10/488672
DATED : July 28, 2009
INVENTOR(S) : Makoto Takano et al.

It is certified that error appears in the above-identified patent and that said Letters Patent is hereby corrected as shown below:

```
<210> 9
<211> 23
<212> DNA
<213> Artificial Sequence

<220>
<223> Description of Artificial Sequence: Synthetic
      primer

<400> 9
gcctaattga gacagcaact gcg                                         23

<210> 10
<211> 20
<212> DNA
<213> Artificial Sequence

<220>
<223> Description of Artificial Sequence: Synthetic
      primer

<400> 10
ttggctgttg acatcactgg                                             20

<210> 11
<211> 24
<212> DNA
<213> Artificial Sequence

<220>
<223> Description of Artificial Sequence: Synthetic
      primer

<400> 11
acgagcttct ggcttatgta aagg                                        24

<210> 12
<211> 23
<212> DNA
<213> Artificial Sequence

<220>
<223> Description of Artificial Sequence: Synthetic
      primer

<400> 12
tggcggaaca tctcttgtat cag                                         23

<210> 13
<211> 24
<212> DNA
<213> Artificial Sequence
```

UNITED STATES PATENT AND TRADEMARK OFFICE
CERTIFICATE OF CORRECTION

PATENT NO. : 7,566,815 B2
APPLICATION NO. : 10/488672
DATED : July 28, 2009
INVENTOR(S) : Makoto Takano et al.

It is certified that error appears in the above-identified patent and that said Letters Patent is hereby corrected as shown below:

```
<220>
<223> Description of Artificial Sequence: Synthetic
      primer

<400> 13
ttggatcttg tatcttgtat atac                                        24

<210> 14
<211> 24
<212> DNA
<213> Artificial Sequence

<220>
<223> Description of Artificial Sequence: Synthetic
      primer

<400> 14
gctaatacta ttgttaggtt gcaa                                        24

<210> 15
<211> 24
<212> DNA
<213> Artificial Sequence

<220>
<223> Description of Artificial Sequence: Synthetic
      primer

<400> 15
ctggacatgg gccaactata cagt                                        24

<210> 16
<211> 24
<212> DNA
<213> Artificial Sequence

<220>
<223> Description of Artificial Sequence: Synthetic
      primer

<400> 16
 attagcttgt atatatattt aaca                                       24

<210> 17
<211> 3980
<212> DNA
<213> Oryza sativa

<400> 17
ggagatatta tcttgggctg ccttgccgtg cagtgtggct cgctgtccca ctcaggtgcg   60
gcgctattcc aatccgtgct tatcccggc agaatccaat ccccctcgcg gcttttctcc  120
```

UNITED STATES PATENT AND TRADEMARK OFFICE
CERTIFICATE OF CORRECTION

PATENT NO. : 7,566,815 B2
APPLICATION NO. : 10/488672
DATED : July 28, 2009
INVENTOR(S) : Makoto Takano et al.

It is certified that error appears in the above-identified patent and that said Letters Patent is hereby corrected as shown below:

```
aaaagcgctc cgccttctcg cctatttcgc tcgctgccgc ggccatgatt ccccgctgat 180
acctccgcgc gcccatttgg ttcctcctcg ccgaatcccc cttcgcagcc ggtggttcta 240
gttgaggagg aggaggaggg gatttggttg ggggcgaggg ggaggagggg gttgtggaga 300
tgtcgtcgtc gcggtcgaac aaccgggcga cgtgctcgcg gagcagctcg gcgcggtcca 360
agcacagcgc gcgggtggtg gcgcagacgc cgatggacgc gcagctgcac gcggagttcg 420
aggggtcgca gcgccacttc gactactcgt cgtcggtggg cgcggccaat cggtcgggcg 480
ccaccaccag caacgtctcc gcctacctcc agaacatgca gcgcggccgc ttcgtccagc 540
ccttcgggtg cctgctcgcc gtccacccgg agacgttcgc gctgctcgcc tacagcgaga 600
acgccgccga gatgctcgac ctcacgccgc acgccgtgcc caccattgac cagcgcgagg 660
cgctcgccgt cggcaccgac gtgcgcacgc tcttccgctc gcacagcttc gtcgcgctgc 720
agaaggccgc caccttcggg gacgtcaacc tgctcaaccc catcctcgtc cacgccagga 780
cctccgggaa gcccttctac gccatcatgc accgcatcga cgtcggcctc gtcatcgacc 840
tcgagccggt caacccgtc gacctgcccg tcaccgccac aggcgcgatc aagtcgtaca 900
agctcgctgc cagggccatc gccaggctgc agtccctgcc cagtgggaac ctctccctgc 960
tgtgcgacgt gctggtccgc gaggtgagcg agctcactgg ctatgacagg gtgatggcgt 1020
acaagttcca tgaggatgag catggtgagg tgattgctga gtgcaagaga tctgatttgg 1080
agccgtatct tggcctgcac tacccagcca ctgacattcc tcaggcatcc aggtttttgt 1140
tcatgaagaa caaagtgcgg atgatatgcg attgctccgc aacgcctgtg aagatcatcc 1200
aagatgacag cctaacacaa cctataagca tatgcggatc tactctcagg gcacccatg 1260
gttgccatgc acagtacatg gcaagcatgg gctccgttgc atcacttgtg atgtcggtca 1320
ctataaatga ggatgaggat gatgatggag acactgggag tgaccagcag ccgaaaggga 1380
ggaagctgtg ggggttgatg gtctgccatc acacaagccc gaggtttgtc cctttcccgc 1440
ttaggtatgc ttgcgagttt ctcttgcaag tatttgggat acagatcaac aaggaggtgg 1500
aactggctgc tcaggcaaag gagaggcaca tcctccgcac gcagactctt ctctgtgata 1560
tgctccttcg agatgctcct gttgggatat ttacccaatc acctaacgta atggatctag 1620
tgaaatgtga tggtgcagca ttgtattacc aaaaccagct ttgggtgcta ggatcaacgc 1680
cctctgaagc agagataaaa aacattgttg cttggttgca ggagtaccat gacggttcta 1740
ctggattgag taccgacagc ttagttgaag caggttatcc tggcgctgct gcacttggtg 1800
atgttgtgtg tggcatggca gctataaaga tctcttcaaa agatttcatc ttctggttcc 1860
gatcccacac ggcaaaggag attaaatggg gaggagctaa gcatgaacca attgatgcag 1920
atgacaatgg taggaagatg catccacgat cttcattcaa agccttcttg gaggtagtta 1980
aatggaggag tgttccttgg gaggatgttg aaatggatgc tatccattct ctgcagctaa 2040
tattacgtgg ctccttgcaa gatgaagatg ccaacaagaa caacaatgca aagtccattg 2100
ttacagctcc atctgatgat atgaagaaga ttcagggggct ccttgaactg agaaccgtta 2160
caaacgagat ggtgcgccta attgagacag caactgcgcc tatcttggct gttgacatca 2220
ctggagcat aaacggatgg aataataagg ctgcagaact cactggatta cctgtcatgg 2280
aagccatagg gaagcctctg gtcgatctcg tcatcgatga ttctgttgaa gtggttaagc 2340
aaatttaaa ttcagcttta caaggaatag aagagcaaaa tctgcaaatt aagcttaaaa 2400
catttaatca ccaggaaaat aatggacctg taattttgat ggttaacgcc tgctgcagtc 2460
gtgacctttc agagaaagtt gtgggggttt gctttgtagc acaagatatg acagggcaga 2520
acattatcat ggataagtac actcggatac aagggggacta tgttgctata gtaaagaacc 2580
cttcggagct catccccct atatttatga tcaatgatct tggttcctgc ttagagtgga 2640
atgaagctat gcaaaaatt actggtataa agagggaaga tgcagtagat aaattgctaa 2700
tcggggaagt tttcacccac catgagtatg gctgtagggt gaaagaccat ggtactctga 2760
ccaaacttag catattaatg aacacagtga tatctggtca agatcctgag aagcttcttt 2820
ttggtttctt caacaccgat ggcaagtaca tagagtcact gatgacagca accaagagga 2880
cagatgctga gggtaagatc actggcgccc tttgctttct tcatgtggcc agcccagagc 2940
ttcaacatgc tctgcaggtg cagaagatgt ctgaacaagc tgctatgaac agctttaagg 3000
aactgacata catacgtcaa gaattaagga acccactcaa tggcatgcaa tttactcgaa 3060
atttgttgga accttctgac ttgactgagg agcagaggaa acttctagca tcaaatgtcc 3120
tctgtcaaga acagctgaaa aagatttac atgacactga tctagaaagc attgaacagt 3180
gctacacgga gatgagcacc gtagatttca acctggagga agccctgaat acagtcctaa 3240
tgcaagccat gccccagagc aaggagaaac aaatttccat tgaccgtgat tggcctgcag 3300
aagtatcatg tatgcacctc tgcggggaca atttaaggct tcaacaagtc ctagcagact 3360
tcctggcatg catgcttcaa tttacacagc cagctgaagg gcctattgtg ctccaagtca 3420
tccccaggat ggaaaatatt ggatctggaa tgcagattgc tcatctagag ttcaggcttg 3480
```

Page 6 of 11

UNITED STATES PATENT AND TRADEMARK OFFICE
CERTIFICATE OF CORRECTION

PATENT NO. : 7,566,815 B2
APPLICATION NO. : 10/488672
DATED : July 28, 2009
INVENTOR(S) : Makoto Takano et al.

It is certified that error appears in the above-identified patent and that said Letters Patent is hereby corrected as shown below:

```
tccatccagc tccgggcgtt ccagaggctc tgatacaaga gatgttccgc cacagcccag 3540
gtgcatctcg agagggcctt ggcctttaca taagccagaa gctcgtgaag acgatgagcg 3600
gcacggttca gtacctccgg gaatcagaga gctcgtcgtt catcgtcctg gtagagttcc 3660
cggtcgccca gctcagcacc aagaggtgca aggcttccac gagtaaattc tgaacttagg 3720
gctatggcca aaattcttgt gggtgctgta ttgttgttgt tgctgctgct gctattagca 3780
gatcaggcag tctgaggagt acgttagctg aagatgtatc agatgtgtgt agcttgtgaa 3840
agtgaaggta gtggttggat agatgtattt gtcacgttga tgtctggaga gctagtgagc 3900
gagctactag gtgttagtgt aatttaaccg gcaaatgtat gaacgaatta tgaataaaat 3960
cttcacttgt gttgtcatga                                             3980
```

<210> 18
<211> 1137
<212> PRT
<213> Oryza sativa

<400> 18

```
Met Ser Ser Ser Arg Ser Asn Asn Arg Ala Thr Cys Ser Arg Ser Ser
 1               5                  10                  15

Ser Ala Arg Ser Lys His Ser Ala Arg Val Val Ala Gln Thr Pro Met
            20                  25                  30

Asp Ala Gln Leu His Ala Glu Phe Glu Gly Ser Gln Arg His Phe Asp
        35                  40                  45

Tyr Ser Ser Ser Val Gly Ala Ala Asn Arg Ser Gly Ala Thr Thr Ser
    50                  55                  60

Asn Val Ser Ala Tyr Leu Gln Asn Met Gln Arg Gly Arg Phe Val Gln
 65                 70                  75                  80

Pro Phe Gly Cys Leu Leu Ala Val His Pro Glu Thr Phe Ala Leu Leu
                85                  90                  95

Ala Tyr Ser Glu Asn Ala Ala Glu Met Leu Asp Leu Thr Pro His Ala
               100                 105                 110

Val Pro Thr Ile Asp Gln Arg Glu Ala Leu Ala Val Gly Thr Asp Val
           115                 120                 125

Arg Thr Leu Phe Arg Ser His Ser Phe Val Ala Leu Gln Lys Ala Ala
       130                 135                 140

Thr Phe Gly Asp Val Asn Leu Leu Asn Pro Ile Leu Val His Ala Arg
145                 150                 155                 160

Thr Ser Gly Lys Pro Phe Tyr Ala Ile Met His Arg Ile Asp Val Gly
               165                 170                 175

Leu Val Ile Asp Leu Glu Pro Val Asn Pro Val Asp Leu Pro Val Thr
           180                 185                 190

Ala Thr Gly Ala Ile Lys Ser Tyr Lys Leu Ala Ala Arg Ala Ile Ala
       195                 200                 205
```

UNITED STATES PATENT AND TRADEMARK OFFICE
CERTIFICATE OF CORRECTION

PATENT NO. : 7,566,815 B2
APPLICATION NO. : 10/488672
DATED : July 28, 2009
INVENTOR(S) : Makoto Takano et al.

It is certified that error appears in the above-identified patent and that said Letters Patent is hereby corrected as shown below:

```
Arg Leu Gln Ser Leu Pro Ser Gly Asn Leu Ser Leu Leu Cys Asp Val
    210             215             220
Leu Val Arg Glu Val Ser Glu Leu Thr Gly Tyr Asp Arg Val Met Ala
225             230             235                         240
Tyr Lys Phe His Glu Asp Glu His Gly Glu Val Ile Ala Glu Cys Lys
                245             250             255
Arg Ser Asp Leu Glu Pro Tyr Leu Gly Leu His Tyr Pro Ala Thr Asp
            260             265             270
Ile Pro Gln Ala Ser Arg Phe Leu Phe Met Lys Asn Lys Val Arg Met
        275             280             285
Ile Cys Asp Cys Ser Ala Thr Pro Val Lys Ile Ile Gln Asp Asp Ser
    290             295             300
Leu Thr Gln Pro Ile Ser Ile Cys Gly Ser Thr Leu Arg Ala Pro His
305             310             315                         320
Gly Cys His Ala Gln Tyr Met Ala Ser Met Gly Ser Val Ala Ser Leu
                325             330             335
Val Met Ser Val Thr Ile Asn Glu Asp Glu Asp Asp Asp Gly Asp Thr
            340             345             350
Gly Ser Asp Gln Gln Pro Lys Gly Arg Lys Leu Trp Gly Leu Met Val
        355             360             365
Cys His His Thr Ser Pro Arg Phe Val Pro Phe Pro Leu Arg Tyr Ala
    370             375             380
Cys Glu Phe Leu Leu Gln Val Phe Gly Ile Gln Ile Asn Lys Glu Val
385             390             395                         400
Glu Leu Ala Ala Gln Ala Lys Glu Arg His Ile Leu Arg Thr Gln Thr
                405             410             415
Leu Leu Cys Asp Met Leu Leu Arg Asp Ala Pro Val Gly Ile Phe Thr
            420             425             430
Gln Ser Pro Asn Val Met Asp Leu Val Lys Cys Asp Gly Ala Ala Leu
        435             440             445
Tyr Tyr Gln Asn Gln Leu Trp Val Leu Gly Ser Thr Pro Ser Glu Ala
    450             455             460
Glu Ile Lys Asn Ile Val Ala Trp Leu Gln Glu Tyr His Asp Gly Ser
465             470             475                         480
Thr Gly Leu Ser Thr Asp Ser Leu Val Glu Ala Gly Tyr Pro Gly Ala
                485             490             495
Ala Ala Leu Gly Asp Val Val Cys Gly Met Ala Ala Ile Lys Ile Ser
            500             505             510
```

UNITED STATES PATENT AND TRADEMARK OFFICE
CERTIFICATE OF CORRECTION

PATENT NO. : 7,566,815 B2
APPLICATION NO. : 10/488672
DATED : July 28, 2009
INVENTOR(S) : Makoto Takano et al.

It is certified that error appears in the above-identified patent and that said Letters Patent is hereby corrected as shown below:

```
Ser Lys Asp Phe Ile Phe Trp Phe Arg Ser His Thr Ala Lys Glu Ile
        515             520                 525

Lys Trp Gly Gly Ala Lys His Glu Pro Ile Asp Ala Asp Asp Asn Gly
    530             535                 540

Arg Lys Met His Pro Arg Ser Ser Phe Lys Ala Phe Leu Glu Val Val
545                 550             555                     560

Lys Trp Arg Ser Val Pro Trp Glu Asp Val Glu Met Asp Ala Ile His
                565             570                 575

Ser Leu Gln Leu Ile Leu Arg Gly Ser Leu Gln Asp Glu Asp Ala Asn
            580             585                 590

Lys Asn Asn Asn Ala Lys Ser Ile Val Thr Ala Pro Ser Asp Asp Met
            595             600                 605

Lys Lys Ile Gln Gly Leu Leu Glu Leu Arg Thr Val Thr Asn Glu Met
        610             615             620

Val Arg Leu Ile Glu Thr Ala Thr Ala Pro Ile Leu Ala Val Asp Ile
625                 630             635                     640

Thr Gly Ser Ile Asn Gly Trp Asn Asn Lys Ala Ala Glu Leu Thr Gly
                645             650                 655

Leu Pro Val Met Glu Ala Ile Gly Lys Pro Leu Val Asp Leu Val Ile
                660             665                 670

Asp Asp Ser Val Glu Val Val Lys Gln Ile Leu Asn Ser Ala Leu Gln
            675             680                 685

Gly Ile Glu Glu Gln Asn Leu Gln Ile Lys Leu Lys Thr Phe Asn His
        690             695             700

Gln Glu Asn Asn Gly Pro Val Ile Leu Met Val Asn Ala Cys Cys Ser
705                 710             715                     720

Arg Asp Leu Ser Glu Lys Val Val Gly Val Cys Phe Val Ala Gln Asp
                725             730                 735

Met Thr Gly Gln Asn Ile Ile Met Asp Lys Tyr Thr Arg Ile Gln Gly
            740             745                 750

Asp Tyr Val Ala Ile Val Lys Asn Pro Ser Glu Leu Ile Pro Pro Ile
            755             760                 765

Phe Met Ile Asn Asp Leu Gly Ser Cys Leu Glu Trp Asn Glu Ala Met
        770             775             780

Gln Lys Ile Thr Gly Ile Lys Arg Glu Asp Ala Val Asp Lys Leu Leu
785                 790             795                     800
```

UNITED STATES PATENT AND TRADEMARK OFFICE
CERTIFICATE OF CORRECTION

PATENT NO. : 7,566,815 B2
APPLICATION NO. : 10/488672
DATED : July 28, 2009
INVENTOR(S) : Makoto Takano et al.

It is certified that error appears in the above-identified patent and that said Letters Patent is hereby corrected as shown below:

```
    Ile Gly Glu Val Phe Thr His His Glu Tyr Gly Cys Arg Val Lys Asp
                    805                 810                 815
    His Gly Thr Leu Thr Lys Leu Ser Ile Leu Met Asn Thr Val Ile Ser
                    820                 825                 830
    Gly Gln Asp Pro Glu Lys Leu Leu Phe Gly Phe Phe Asn Thr Asp Gly
                    835                 840                 845
    Lys Tyr Ile Glu Ser Leu Met Thr Ala Thr Lys Arg Thr Asp Ala Glu
        850                 855                 860
    Gly Lys Ile Thr Gly Ala Leu Cys Phe Leu His Val Ala Ser Pro Glu
    865                 870                 875                 880
    Leu Gln His Ala Leu Gln Val Gln Lys Met Ser Glu Gln Ala Ala Met
                    885                 890                 895
    Asn Ser Phe Lys Glu Leu Thr Tyr Ile Arg Gln Glu Leu Arg Asn Pro
                    900                 905                 910
    Leu Asn Gly Met Gln Phe Thr Arg Asn Leu Leu Glu Pro Ser Asp Leu
                    915                 920                 925
    Thr Glu Glu Gln Arg Lys Leu Leu Ala Ser Asn Val Leu Cys Gln Glu
                    930                 935                 940
    Gln Leu Lys Lys Ile Leu His Asp Thr Asp Leu Glu Ser Ile Glu Gln
    945                 950                 955                 960
    Cys Tyr Thr Glu Met Ser Thr Val Asp Phe Asn Leu Glu Glu Ala Leu
                    965                 970                 975
    Asn Thr Val Leu Met Gln Ala Met Pro Gln Ser Lys Glu Lys Gln Ile
                    980                 985                 990
    Ser Ile Asp Arg Asp Trp Pro Ala Glu Val Ser Cys Met His Leu Cys
                    995                 1000                1005
    Gly Asp Asn Leu Arg Leu Gln Gln Val Leu Ala Asp Phe Leu Ala Cys
    1010                1015                1020
    Met Leu Gln Phe Thr Gln Pro Ala Glu Gly Pro Ile Val Leu Gln Val
    1025                1030                1035                1040
    Ile Pro Arg Met Glu Asn Ile Gly Ser Gly Met Gln Ile Ala His Leu
                    1045                1050                1055
    Glu Phe Arg Leu Val His Pro Ala Pro Gly Val Pro Glu Ala Leu Ile
                    1060                1065                1070
    Gln Glu Met Phe Arg His Ser Pro Gly Ala Ser Arg Glu Gly Leu Gly
                    1075                1080                1085
    Leu Tyr Ile Ser Gln Lys Leu Val Lys Thr Met Ser Gly Thr Val Gln
                    1090                1095                1100
```

UNITED STATES PATENT AND TRADEMARK OFFICE
CERTIFICATE OF CORRECTION

PATENT NO. : 7,566,815 B2
APPLICATION NO. : 10/488672
DATED : July 28, 2009
INVENTOR(S) : Makoto Takano et al.

It is certified that error appears in the above-identified patent and that said Letters Patent is hereby corrected as shown below:

```
Tyr Leu Arg Glu Ser Glu Ser Ser Phe Ile Val Leu Val Glu Phe
1105              1110              1115             1120

Pro Val Ala Gln Leu Ser Thr Lys Arg Cys Lys Ala Ser Thr Ser Lys
                1125             1130              1135

Phe
                                                                --.
```

Signed and Sealed this

First Day of December, 2009

David J. Kappos
*Director of the United States Patent and Trademark Office*